United States Patent [19]
Snyder

[11] Patent Number: 5,462,066
[45] Date of Patent: Oct. 31, 1995

[54] SNORING RELIEF DEVICE

[76] Inventor: David T. Snyder, 4007 Pretense Ct., Fair Oaks, Calif. 95628

[21] Appl. No.: 196,009

[22] Filed: Feb. 10, 1994

[51] Int. Cl.⁶ ................................................ A61F 5/37
[52] U.S. Cl. ......................... 128/848; 128/861; 128/862
[58] Field of Search ............................ 128/848, 858, 128/859, 860, 861, 862, 62 A; 2/2

[56] References Cited

U.S. PATENT DOCUMENTS

| | | | |
|---|---|---|---|
| 1,674,336 | 6/1928 | King | 128/848 |
| 2,424,533 | 7/1942 | Faires | 128/848 |
| 2,574,623 | 11/1951 | Clyde | 128/848 |
| 2,627,268 | 2/1953 | Leppich | 128/848 |
| 3,295,519 | 1/1967 | Gerber | 128/860 |
| 3,411,501 | 11/1968 | Greenburg | 128/862 |
| 5,092,346 | 3/1992 | Hays | 128/848 |
| 5,117,816 | 6/1992 | Shapiro | 128/848 |
| 5,277,202 | 1/1994 | Hays | 128/848 |
| 5,277,203 | 1/1994 | Hays | 128/861 |

*Primary Examiner*—Michael A. Brown
*Attorney, Agent, or Firm*—Mark C. Jacobs

[57] ABSTRACT

An anti-snore device, which includes a U-shaped thermoplastic mouthpiece, moldable to fit the jaw definition of the wearer which device has a generally H-shaped cross section, with rearwardly diminishing elevations of the outer and inner vertical walls, both above and below the base to which these walls are attached. The outer wall features front facing opposed upper concave and lower convex areas. The device also includes a downwardly extending flange which extends into the lingual or tongue side of the teeth vestibule of the user to maintain the lower jaw in a forward posture. An optional removable handle of similar thermoplastic material to aid the custom molding process for the fit to the wearer may be employed.

9 Claims, 2 Drawing Sheets

SNORING RELIEF DEVICE

BACKGROUND OF THE INVENTION

Snoring takes place when the uvula and the soft palate at the rear of the mouth vibrate in response to the flow of air past these tissues. It may be caused by any of nasal congestion, the tone of the muscles supporting the soft palate, or large tonsils. Age, alcohol and additional body weight can negatively impact a snorer's condition by weakening muscle tone.

In the 1960's it was thought that snoring could be minimalized or even eliminated if the air flow thorough the mouth was inhibited. Therefore anti-snore devices of that era were constructed to block the flow of air through the mouth such that the breather had to inhale and exhale through the nose. The hoped for result was that the tissue that was vibrating as air passed over it would not do so since less air was moving past the tissues. Devices constructed to operate based on this theory failed to gain significant market acceptance because they were cumbersome and uncomfortable to the wearers.

The earliest surgical procedures merely provided for removal of the tonsils. This was helpful to some of the approximately twenty plus million snorers in the U.S.A. alone. Since the sixties, throat surgical procedures have been developed which comprise cutting part of the uvula to eliminate the vibration and therefore deter snoring. These and other surgical procedures have also been utilized to overcome the more serious problem of sleep apnea. This is a transient cessation of breathing during one's sleep.

Sleep apnea is a condition that can arise after one becomes a snorer. It is a condition that results in frequent repetitive pauses in breathing during sleep. It arises from the presence of an abnormally small air passage at the junction of the tonsils and soft palate. A turbulence is created which is responsible for the snoring and which makes breathing more difficult. While the apnea itself is not a crisis problem, apnea can detrimentally affect the blood pressure, which can result in heart attack and heart failure.

While applicant did suffer from sleep apnea, he did undergo multithousand dollar throat surgery for snoring relief, only to find that the surgical benefits were of short duration. Not to mention, the discomfort associated with the recovery period.

Medical experts today, contrary to the thinking of the 1960's, believe that for certain patients, if the snorer's lower jaw is moved forward during sleep time to thereby add tone to the throat muscles and to open the air passageway, not restrict it, snoring can be reduced or eliminated. Thus today these mouth appliances are made available to the public at sleep disorder centers and by dentists through out the U.S.A. That is the upside! The downside is that many people cannot afford the $300 to $600 cost and the time associated with being fitted for these custom made appliances.

There is a need therefore for a low cost device that can be easily fitted by the wearer, that will both reduce the cost of purchase and eliminate the loss of time associated with custom made dental appliances.

Prior to making the instant invention, applicant caused an extensive patent search to be carried out to determine the state-of-the-art in mouth pieces. These seem to fall into two categories; namely, those used by athletes such as the football players many of us see on television each Saturday and Sunday which serve as a tooth guard; and those devices used to inhibit snoring. The following references turned up during the course of the search:

| # | Patent No. | Applicant | Patent Type |
|---|---|---|---|
| 1. | 2,669,988 | Carpenter | TP |
| 2. | 3,312,218 | Jacobs | TP |
| 3. | 3,434,470 | Strickland | SI |
| 4. | 3,478,742 | Bohlmaann | OTHER |
| 5. | 4,304,227 | Samelson | SI |
| 6. | 4,568,280 | Ahlin | OTHER |
| 7. | 4,593,686 | LLoyd et al | SA |
| 8. | 4,715,368 | George | SA |
| 9. | D-302,036 | George | SA |
| 10. | 4,848,365 | Guarlotti et al | TP |
| 11. | 5,018,533 | Hawkins | SA |
| 12. | 5,003,994 | Cook | SI |
| 13. | 5,042,506 | Liberate | SI/SA |
| 14. | 5,046,512 | Murchie | SI/SA |
| 15. | 5,056,534 | Wright | SI |
| 16. | 5,092,346 | Hays et al | SI |
| 17. | 5,117,816 | Shapiro et al | SI |

WHEREIN "TP" means Tooth Protector; "SI" means Snore Inhibitor, and "SA" pertains to Sleep Apnea.

Of the references cited above, of all types, no one reference, or any combination thereof anticipates the subject matter of this application or renders the invention obvious in light of prior art.

It is first object therefore to provide a snore inhibiting device that is custom fit to the wearer, but is low in cost.

A second object is to provide a snore inhibiting device which incorporates modern medical thinking.

Another object is to provide a dental mouthpiece which during periods of sleep retains the lower jaw in a forward position.

Still another object is to provide a dental mouthpiece that can be made pliable upon being subjected to hot water such that it can be custom fit, which custom fit will be retained upon cooling of the device.

Yet another object is to provide a tooth covering device that can be readily molded to conform to the bite of the individual wearer.

A yet further object is to provide a custom moldable mouthpiece with a removable handle thereupon.

Still another object is provide a colorful dental appliance which resists being misplaced.

An additional object is to provide a device which can be worn comfortably by the wearer.

Other objects of the invention will in part be obvious and will in part appear hereinafter.

The invention accordingly comprises the device possessing the features properties and the relation of components which are exemplified in the following detailed disclosure and the scope of the application of which will be indicated in the appended claims.

For a fuller understanding of the nature and objects of the invention reference should be made to the following detailed description, taken in conjunction with the accompanying drawings.

SUMMARY OF THE INVENTION

An anti-snore device, which also reduces the possible onset of sleep apnea, which device comprises a U-shaped thermoplastic mouthpiece, individually custom moldable to fit the jaw definition of the wearer which has a generally H-shaped cross section, with rearwardly diminishing elevations of the outer and inner vertical walls, both above and below the base to which these walls are attached to define the H-shaped cross section. The outer wall features front facing opposed upper concave and lower convex areas. A downwardly extending flange with a rearwardly directed incisal region extends into the lingual or tongue side of the teeth vestibule of the user serves to maintain the lower jaw in a forward posture.

The device may include a removable handle of similar thermoplastic material which is used to aid the initial warm molding process for the initial fit to the wearer.

DESCRIPTION OF THE PREFERRED EMBODIMENT

Device 10 is seen in FIGS. 1–5 as received by the proposed user prior to custom molding to fit his or her mouth. The discussion will therefore relate to the generalized device with information on how to mold it into a specific user device to follow.

Figure 1:
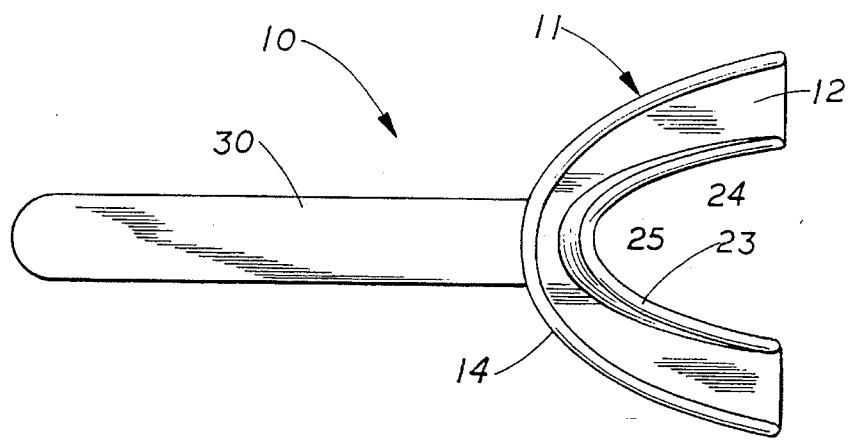
FIG. 1 is a bottom plan view of the device of this invention, prior to custom molding to fit.
Figure 2:
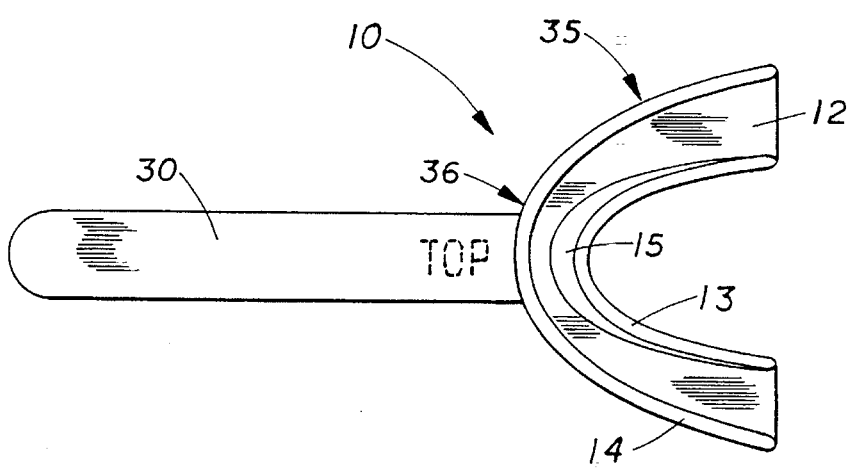
FIG. 2 is a top plan view thereof.

Device 10 as seen in FIG. 1, a bottom plan view, and FIG. 2, the top plan view, comprises a molded generally U-shaped channel member 11 adapted to be clamped between the teeth of the upper and lower jaw when positioned for use in the mouth. A forwardly extending flexible tab 30 is attached to this channel member 11. Channel 11 includes an inner wall 13, and a spaced outer wall 14, both of which are attached to a base 12 and extend increasingly upwardly therefrom toward the front of the device above the base, and increasingly downwardly therefrom toward the front of the device below the base. See also FIG. 4.

Figure 4:
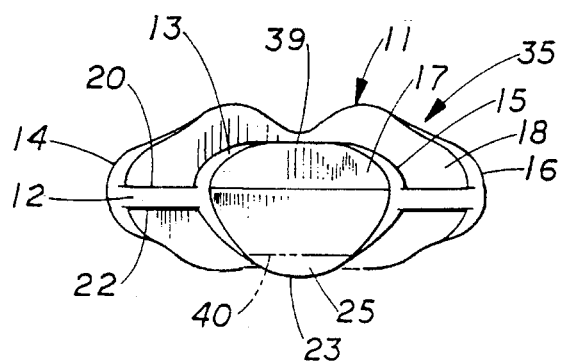
FIG. 4 is a rear elevation of the anti-snore device of this invention.
Figure 5:
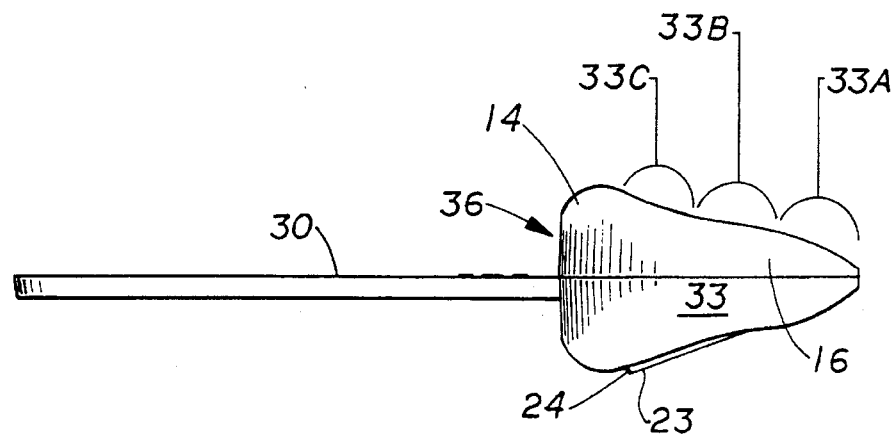
FIG. 5 is a left side elevational view of this invention. The right side view (not shown) is a mirror image of this Figure.

From the underside or bottom plan view of FIG. 1, and from FIG. 5, one notes the presence of a flange 23, on channel 11 to be explained in more detail infra. One also notes from reference made to FIG. 4 and FIG. 5, that the inner and outer walls are configured with a slight curve to generally conform to the contour of the mouth of a user.

Figure 3:
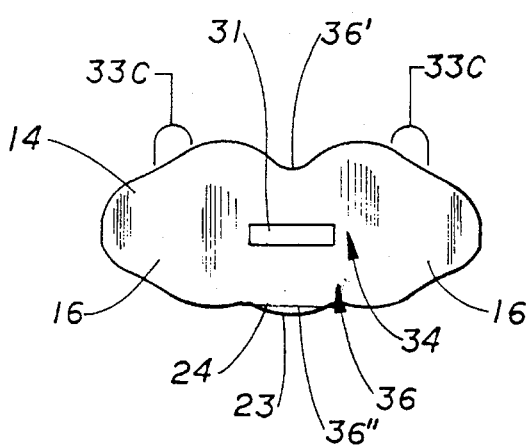
FIG. 3 is a front elevational view of the device of this invention with the fit tab removed.

In FIG. 3, a front elevational view, there is shown the exterior surface 16 of the outer wall 14 and the exterior surface 25 of the flange 23. Tab remnant 31, represents the flattened cross-sectional area that remains after tab 30 is removed following the molding cycle to be discussed below. This remnant can be heat polished to blend out any deviations from the general contour of the exterior surface 16. The front segment of the outer wall designated 36 is seen in several views.

As seen in FIGS. 2 and 3, the channel member 11 is arcuate and includes a left curved section 33, a front section 36 of a width slightly greater than the width of the tab remnant 31 and a right curved section 35. See FIG. 2.

Reference should now be made to FIG. 5, where it is seen that the outer wall 14, has a unique configuration. The side sections, only one of which will be discussed in detail is shown in this FIG. 5 and is seen to include three segments, the edges of which will be recited. The first is a rear segment 33A, that commences at the rear of the base and tapers both upwardly and downwardly at a first angle in each direction to achieve a first height, a central segment 33B which is at first nearly flat on the top surface and then tapering upwardly to a maximum incline, while on the bottom diverging downwardly at an angle greater than segment 33A. Segment 33C commences at the terminus of 33B and is directed convexly at the top and concavely at the bottom to a point of maximum separation as the exterior surface 16 of outer wall 14 curves forwardly. See FIG. 1. The other side, 35, is a mirror image of side 33.

The front region of the device, designated 36 commences at the termination of the segments 33C, as per FIG. 3. Obviously the lines of demarcation between each of the segments 33A, B and C and 36 the front is arbitrary and completely subjective. Front region 36 commences at the points of maximum elevation of the upper edge and minimum elevation of the lower edge of the outer wall, which has been defined supra as the termini of segments 33C and forms a concave area 36' on the top edge and a flat area 36" on the bottom edge between these termini of segment 33C.

In FIG. 4, the rear elevational view, the channel member 11 is seen to be of a somewhat H-shaped cross section, wherein base 12 is seen to be a flat generally U-shaped member which has an upper surface 20 and a lower surface 22. Channel 11's outer side wall 14 with its exterior surface 16 and interior surface 18, and its inner side wall 13 with its respective interior surface 15 and exterior surface 17 are best seen in this FIG. 4. These side walls each diverge from their point of commencement at the rearmost edges of the U-shaped base in a generally normal orientation to the base 12, to give rise to the somewhat H-shaped cross section of the channel member 11. The elevation of each of the segments of the inner wall 13, is somewhat different as can be seen in FIG. 4. This is due to the inclusion of the downwardly depending triangular shaped flange 23.

The upper edge on both sides of the inner wall 13 includes a first segment that rises on an incline to a point of maximum elevation and then stays constant throughout the entire arcuate central segment, 39, per FIG. 4. The lower edge but for the presence of the flange is similarly configured.

In FIGS. 3 and 4, flange 23 with its interior surface 24 and its exterior surface 25 is seen. This flange is integral with and depends downwardly and rearwardly at its incisal region from what would be the artificial line 40 which defines the bottom edge of interior wall 13. See also FIG. 5, wherein from the side vantage point, the flange sticks below the outer side wall, but the inner wall at the top with no flange does not peek above the outer sidewall.

This configuration with the hill and valley in the front of the device was chosen after much research effort, as this configuration helps to achieve maximum conformation with the outline of the teeth pressing vertically and eases the ability of the device to be curved to the specific contours of the mouth of the wearer during the molding cycle discussed below.

HEAT TREATMENT FOR CUSTOM FIT TO USER

The snoring relief device of this invention is intended to be molded to the mouth of the specific user. The preferred material employed is one readily adapted to receive a dental impression which conforms to the shape of the teeth and surrounding gum tissue of the wearer, quickly and easily. The method employed by the user requires no special training to secure a good fit.

It is highly recommended that since the preferred material, is a member of the Elvax® resin family (copolymers of ethylene and vinyl acetate) sold by E. I. DuPont is a thermoplastic resin, sufficient care should be taken to try to ensure that a correct fit is achieved on the first or preferably no later than the second attempt. Though further reheatings are possible there may be some configuration degradation with repeated heating and reshaping after the third attempt.

Therefore it is deemed beneficial prior to actually heating device 10 to custom mold it, to place the device into the mouth of the wearer, close one's lips, and practice sucking the air out of your mouth while pressing the tongue all around the exterior surface, 17 of the inner wall. See FIG. 4. Simultaneously the user should press with the fingers upon the lips. The result is that the teeth of the lower jaw move into position within the device—the upper teeth are already there upon insertion into the mouth—such that the lower jaw projects forwardly. The incisor teeth (front teeth) are aligned. Once this learning procedure is mastered, the user is ready for the real custom fitting process.

One should heat about 12–16 ounces (1.5 to 2 cups) of water in a small sauce pan or in a microwave oven vessel until vigorous boiling is achieved. Move the vessel with the heated water to a counter top. Correctly orient the unit 10, by observing the indicia on the tab. One holds the tab between the fingers, or with kitchen tongs, and lowers the channel member 11 into the hot water for a count of about 13 seconds for my preferred material. This first step heats the channel member 11, to a temperature much higher than body temperature at which the device's material will soften and become moldable under moderate pressure.

The actual length of time that the channel member remains in the boiling water may typically range from about 5 to 60 seconds, and will vary with the vinyl acetate content of the copolymer with ethylene.

Care should be exercised that the channel member is not heated to a temperature so high that it will burn the soft tissue of the mouth when inserted therein.

After it has been immersed in the boiling water a sufficient length of time to raise its temperature to the desired level, the channel member 11 is removed from the hot water, preferably with the tongs, or other suitable means. If the unit has been overheated, it should be allowed to cool slightly until it can be placed in the mouth without causing discomfort or burning. After checking the orientation, the device is placed immediately while somewhat soft and pliable into the mouth around the upper and lower teeth as discussed above. Make sure that the rear teeth, both upper and lower are correctly positioned within the channel member 11 by moving the jaw forwardly. Then create a suction by pressing the tongue against the exterior surface inner wall 13, to force the inner wall against the teeth. Start in the middle of the bottom of the unit, by pressing against the flange 23's interior surface 25 and press all around. In a few seconds, while pressing the flange 23, firmly into position with the tongue, and at the same time sucking all of the air and water out of the channel member to draw it tightly against the teeth, one should simultaneously press the fingers on the outside of the lips, keeping the jaw forward to thereby custom mold the dental impression of the teeth and surrounding gum tissue into the channel member 11. The device may then be removed while it is cooling, and preferably placed in a cold water vessel to set the impression and configuration of the unit for retention.

The device will then be custom fit to the mouth of the wearer. The upper 20 and lower 22 surfaces of the base 12 and the adjacent surfaces of the inner and outer walls, will bear a distinct impression of the wearer's teeth. This tooth and soft tissue impression will last indefinitely during usage.

If the fit and finish is not satisfactory to the user, then the unit can again be heated to a temperature above body temperature at which time it can be easily remolded. If the fit becomes loose after extended usage, the device 10 may be re-fit to the wearer's teeth by simply repeating the procedure involved. Caution should be exercised to slightly reduce the dwell time in the boiling water on the second go-round.

Figure 6:
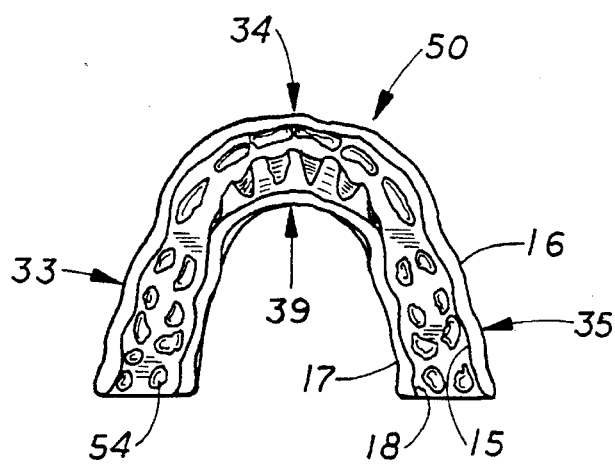
FIG. 6 is a top plan view of a custom molded device for a particular individual.
Figure 7:
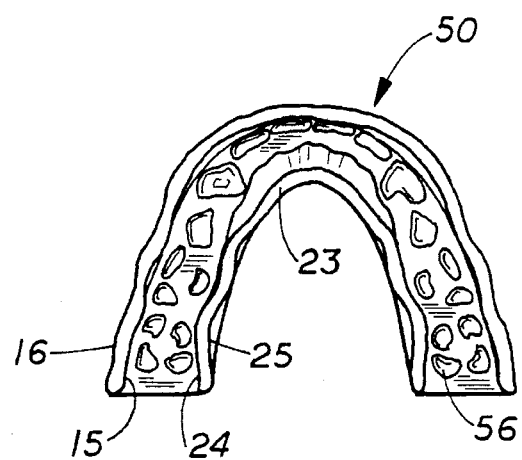
FIG. 7 is a bottom plan view of the custom molded device as seen in FIG. 6.

Reference should be made to FIGS. 6 and 7, the top and bottom plan views of the device in its heat-treated condition 50 which show the upper teeth and lower teeth impressions 54, 56 respectively.

While other mouthpieces such as are used by football players are known to the art and have been cited above, and other attempts to devise a snoring relief device have also been cited and discussed, the unit of this invention is believed to have been specifically engineered to help eliminate snoring and sleep apnea. While other Elvax™ resin structures are known, none include retaining channels for both the upper and lower teeth coupled with the downwardly depending flange which depends below the elevation of the outer wall and which serves to retain the lower teeth in position during sleep when the lower jaw relaxes. It is during sleep that the lower jaw wants to return to its rearward normal location. But in order to alleviate the snoring problem, the lower jaw must be kept forward to open up the air passage way as has been discussed infra. The presence of the frontal hill and valley recesses in the outer wall have been found to aid the wearer achieve better customization of the device to his or her mouth.

While no medical claim is made, it is believed that the overall rearwardly tapered configuration of the inner wall tends to reduce the amount of saliva generation. In addition, the relative lack of bulk in this appliance, permits the user's lips to achieve a closed condition, which condition thereby stops saliva from drooling out of the mouth, as so often happens with other prior art appliances. The smooth exterior (rear facing) surface of the inner wall and the lack of holes therein provides for an overall more comfortable fit. That is because unconsciously, one's tongue will rub over any surface irregularity such as a "breathing bore", and become sore. And, a further point, the so called breathing holes of certain prior art appliances, tend to increase drooling and dry mouth.

It was indicated that a colorful appliance was one object of this invention. While the normal color of the resin preferred for the manufacture of this product is water white, the addition of food grade dye to the resin during initial manufacture will permit the preparation of violet, teal and other fashion color appliances as may be desired by the marketplace.

While various Elvax™ resins exist, all of which differ in content of vinyl acetate, I prefer to employ an ethylene-vinyl acetate copolymer wherein the vinyl acetate constitutes between 25% and 33% by weight.

While Elvax™ resins are the preferred material for the manufacture of the device of this invention, any material which may be molded at a temperature higher than body temperature, but lower than a temperature which will burn the tongue and surrounding mouth tissue in order to conform to the wearer's dental impression and the surrounding mouth tissue, may be employed.

Since certain changes may be made in the described device without departing from the scope of the invention herein involved, it is intended that all matter contained in the above description and shown in the accompanying drawings shall be interpreted as illustrative and not in a limiting sense.

I claim:

1. A dental device for removable placement in the mouth of a wearer to inhibit snoring and sleep apnea, which device is made from any material which may be molded at a temperature higher than body temperature, but lower than a temperature which will burn the tongue and surrounding mouth tissue in order to conform said device to the wearer's dental impression and the surrounding mouth tissue, and which is adapted to fit around the wearer's teeth and surrounding gum tissue, and which device is further adapted to retain the lower jaw in a forward position during periods of sleep, which device comprises:

an outer wall spaced from an inner wall both of which are attached to a base to define a generally U-shaped channel member as seen from bottom and as seen from the top, said channel member's outer and inner walls when taken with said base define an H-shaped member in elevation wherein, each of said outer and inner walls have rearwardly diminishing elevations along said H-shape, both above and below the base;

said outer wall having a front region, which includes opposed upper concave and lower convex areas.

2. In the device of claim 1 further wherein the inner and outer walls have a slight built in curvature.

3. The device of claim 1 wherein the device is made from a copolymer of ethylene and vinyl acetate.

4. The device of claim 1 further including a removable forward extending tab adapted to aid in the ultimate molding to the dental impression of the wearer.

5. In the device of claim 1 wherein the left and right sections of the outer wall include three segments, the edges of which are defined as follows:

the first or rear segment commences at the rear of the base and tapers both upwardly and downwardly at a first angle in each direction to achieve a first height;

a second central segment which is flat on the top surface and which tapers upwardly to a maximum incline from said first segment to the commencement of said third segment, while the bottom surface thereof, which is also flat diverges downwardly at an angle from said first segment to said third segment, and the third segment commences at the terminus of said second segment and is directed convexly at the top, to a point of maximum separation and is flat across the bottom front as the exterior surface of said outer wall curves forwardly.

6. In the device of claim 5 wherein the downward diverging angle of the bottom surface of the said second segment is different from the downward diverging angle of said first segment.

7. In the device of claim 1 further including a downwardly directed flange of rearwardly diminishing elevation integrated into and extending from the lower inner wall.

8. In the device of claim 1 wherein the downwardly directed flange has an incisal region which is slightly rearwardly directed.

9. In the device of claim 1 including a removable forward extending tab adapted to aid in the ultimate molding of the dental impression of the wearer, and wherein the downward diverging angle of the bottom surface of the said second segment is different from the diverging downward angle of said first segment.

* * * * *